(12) United States Patent
Ehman et al.

(10) Patent No.: US 8,281,663 B2
(45) Date of Patent: Oct. 9, 2012

(54) ACTIVE ACOUSTIC DRIVER FOR MAGNETIC RESONANCE ELASTOGRAPHY

(75) Inventors: Richard L. Ehman, Rochester, MN (US); Phillip J. Rossman, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 365 days.

(21) Appl. No.: 12/502,076

(22) Filed: Jul. 13, 2009

(65) Prior Publication Data

US 2010/0005892 A1 Jan. 14, 2010

Related U.S. Application Data

(63) Continuation-in-part of application No. 12/418,204, filed on Apr. 3, 2009.

(60) Provisional application No. 61/080,446, filed on Jul. 14, 2008, provisional application No. 61/080,420, filed on Jul. 14, 2008.

(51) Int. Cl.
*G01M 7/00* (2006.01)
*G01V 3/00* (2006.01)
*A61B 5/05* (2006.01)

(52) U.S. Cl. ............. 73/662; 73/646; 324/318; 600/415

(58) Field of Classification Search ................... 73/662, 73/646; 324/318, 319; 600/410, 415, 438
See application file for complete search history.

(56) References Cited

U.S. PATENT DOCUMENTS

| 5,010,878 | A | | 4/1991 | Kline et al. |
| 5,606,971 | A | | 3/1997 | Sarvazyan |
| 5,714,722 | A | * | 2/1998 | Noponen ...................... 181/173 |
| 5,810,731 | A | | 9/1998 | Sarvazyan et al. |
| 5,886,264 | A | * | 3/1999 | Hu et al. .......................... 73/646 |
| 5,952,828 | A | * | 9/1999 | Rossman et al. ............... 324/318 |
| 5,977,770 | A | | 11/1999 | Ehman |
| 6,037,774 | A | | 3/2000 | Felmlee et al. |
| 6,486,669 | B1 | | 11/2002 | Sinkus et al. |
| 6,778,677 | B2 | * | 8/2004 | Coffin ........................... 381/418 |
| 6,810,751 | B2 | * | 11/2004 | Moreno et al. ................... 73/849 |
| 7,002,347 | B2 | | 2/2006 | Feiweier et al. |

(Continued)

OTHER PUBLICATIONS

Pneumatically Actuated Driver for Use in MRE of the Brain; 2006; 1 page; no author.

(Continued)

*Primary Examiner* — J M Saint Surin
(74) *Attorney, Agent, or Firm* — Quarles & Brady, LLP

(57) ABSTRACT

A driver for applying an oscillating stress to a subject undergoing a medical imaging procedure, such as with magnetic resonance elastography (MRE), includes a passive driver located in the bore of the magnet and in direct contact with the skin of the subject. A remotely located active driver includes a linear motor and a sealed diaphragm that produces acoustic pressure waves in response to an applied current. The pressure waves are directed through a tube and into a chamber formed within the passive driver. Vibrations produced in response to the pressure waves create shear waves that are directed into the subject to aid in the imaging procedure.

19 Claims, 4 Drawing Sheets

U.S. PATENT DOCUMENTS

| | | |
|---|---|---|
| 7,034,534 B2 | 4/2006 | Ehman et al. |
| 7,278,963 B2 | 10/2007 | Schneider et al. |
| 7,307,423 B2 | 12/2007 | Ehman et al. |
| 7,472,604 B2 * | 1/2009 | Moore et al. .................. 73/849 |
| 2003/0149359 A1 | 8/2003 | Smith |
| 2003/0210811 A1 | 11/2003 | Dubowsky et al. |
| 2005/0018868 A1 | 1/2005 | Chick et al. |
| 2005/0157900 A1 | 7/2005 | Litovsky et al. |
| 2005/0196012 A1 | 9/2005 | Babb et al. |
| 2006/0012367 A1 | 1/2006 | Meaney et al. |
| 2006/0189868 A1 | 8/2006 | Gleich et al. |
| 2006/0241432 A1 | 10/2006 | Herline et al. |
| 2007/0156156 A1 | 7/2007 | Badie |

OTHER PUBLICATIONS

Olivier Rouviere et al; MR Elastography of the Liver: Preliminary Results; Radiology; vol. 240; No. 2-Aug. 2006; pp. 440-448.

Meng Yin et al; Assessment of Hepatic Fibrosis With Magnetic Resonance Elastography; Clinical Gastroenterology and Hepatology 2007; 5:1207-1213.

Bensamoun et al., Determination of Thigh Muscle Stiffness Using Magnetic Resonance Elastography, Journal of Magnetic Resonance Imaging, 2006, 23:242-247.

* cited by examiner

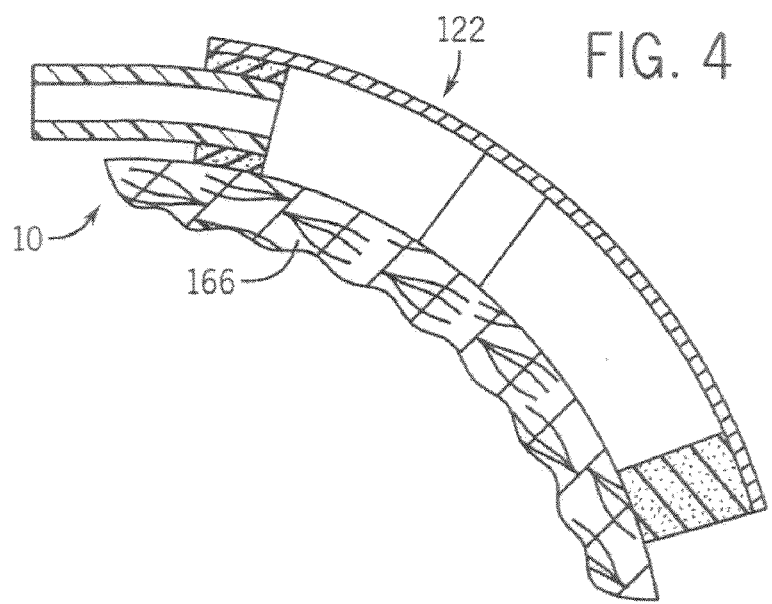
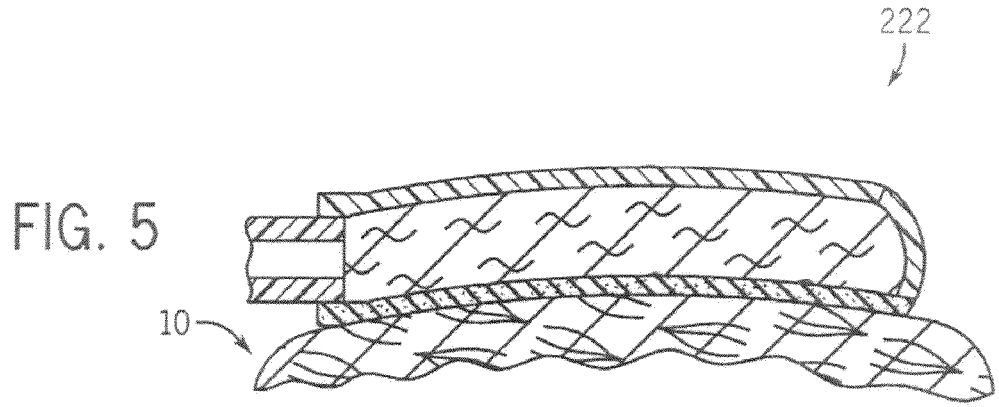

ACTIVE ACOUSTIC DRIVER FOR MAGNETIC RESONANCE ELASTOGRAPHY

CROSS-REFERENCE TO RELATED APPLICATIONS

This application is based on, claims the benefit of, and incorporates by reference U.S. Provisional Application Ser. No. 61/080,446 filed Jul. 14, 2008, and entitled "ACTIVE ACOUSTIC DRIVER FOR MAGNETIC RESONANCE ELASTOGRAPHY," U.S. Provisional Application Ser. No. 61/080,420 filed Jul. 14, 2008, and entitled "PASSIVE ACOUSTIC DRIVER FOR MAGNETIC RESONANCE ELASTOGRAPHY", and this application is a continuation-in-part of U.S. patent application Ser. No. 12/418,204, entitled "Passive Acoustic Driver For Magnetic Resonance Elastography" filed on Apr. 3, 2009.

STATEMENT REGARDING FEDERALLY SPONSORED RESEARCH

This invention was made with government support under Grant No. EB001981 awarded by the National Institutes of Health. The United States Government has certain rights in this invention.

BACKGROUND OF THE INVENTION

The field of the invention is nuclear magnetic resonance imaging methods and systems. More particularly, the invention relates to devices for implementing magnetic resonance elastography (MRE).

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging (MRI) systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient a physician can feel differences in the compliance of tissues and detect the presence of tumors and other tissue abnormalities. Unfortunately, this valuable diagnostic tool is limited to those tissues and organs which the physician can feel, and many diseased internal organs go undiagnosed unless the disease happens to be detectable by one of the above imaging modalities. Tumors (e.g., of the liver) that are undetected by existing imaging modalities and cannot be reached for palpation through the patient's skin and musculature, are often detected by surgeons by direct palpation of the exposed organs at the time of surgery. Palpation is the most common means of detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

It has been found that MR imaging can be enhanced when an oscillating stress is applied to the object being imaged in a method called MR elastography. The method requires that the oscillating stress produce shear waves that propagate through the organ or tissues to be imaged. These shear waves alter the phase of the MR signals, and from this the mechanical properties of the subject can be determined. In many applications, the production of shear waves in the tissues is merely a matter of physically vibrating the surface of the subject with an electromechanical device such as that disclosed in above-cited U.S. Pat. No. 5,592,085. For example, shear waves may be produced in the breast and prostate by direct contact with the oscillatory device. Also, with organs like the liver, the oscillatory force can be directly applied by means of an applicator that is inserted into the organ.

A number of driver devices have been developed to produce the oscillatory force needed to practice MRE. As disclosed in U.S. Pat. Nos. 5,977,770, 5,952,828, 6,037,774, and 6,486,669, these typically include a coil of wire through which an alternating current flows. This coil is oriented in the polarizing field of the MRI system such that it interacts with the polarizing field to produce an oscillating force. This force may be conveyed to the subject being imaged by any number of different mechanical arrangements. Such MRE drivers can produce large forces over large displacement, but they are constrained by the need to keep the coil properly aligned with respect to the polarizing magnetic field. In addition, the current flowing in the driver coil produces a magnetic field which can alter the magnetic fields during the magnetic resonance pulse sequence resulting in undesirable image artifacts.

Another approach is to employ piezoelectric drivers as disclosed in U.S. Pat. Nos. 5,606,971 and 5,810,731. Such drivers do not produce troublesome disturbances in the scanner magnetic fields when operated, but they are limited in the forces they can produce, particularly at larger displacements. Piezoelectric drivers can also be oriented in any direction since they are not dependent on the polarizing magnetic field direction for proper operation.

Yet another approach is to employ an acoustic driver system as described in U.S. Pat. Nos. 7,034,534 and 7,307,423. The system includes a remotely located active acoustic driver acoustically coupled to one or more passive acoustic drivers positioned on the subject being imaged. The active driver includes a loudspeaker cone coupled to a ported cover. The ported cover is constructed of a rigid material such as polycarbonate and has a thin, rectangular shape. Acoustic, or pressure, waves generated by the loudspeaker cone are directed to the passive driver via a tube. In response, shear waves are produced by the passive driver and projected into the subject being imaged. The passive driver and tube do not disturb the magnetic fields and may be oriented in any direction.

This acoustic driver system has been shown to reliably generate shear waves during an MR elastography examination to obtain shear stiffness images, or elastograms. However, the shear waves produced by the passive driver are not strong enough to produce high resolution elastograms. This is especially true, for example, when imaging organs or regions that are large or are located deeper within the body. In other words, when heavy loading of the passive driver is required, such as in MRE imaging of the liver, the resulting elastograms do not have a desired degree of clarity or resolution. Attempts were made to improve the performance of the prior art acoustic driver system by applying higher levels of electrical power and using speaker units with more powerful voice coil motors. However, these attempts did not yield a sufficient improvement over the existing active driver design.

It was determined that these improvements did not improve the performance of the acoustic driver system because loudspeaker cones are designed for driving pressure waves through a low impedance medium such as free air. Acoustically coupling the active driver to the passive driver necessarily seals air within the drivers, thereby creating a high impedance medium. As such, acoustic waves lose energy while traveling through the sealed system. Attempting to produce pressure waves at higher energy levels fails, primarily due to flexing of the speaker cone caused by the sealed nature of the acoustic driver system.

SUMMARY OF THE INVENTION

The present invention is an acoustic driver system which can produce large forces over large displacements without interfering with the energy produced by various medical imaging systems and which may be oriented in any direction on the subject.

More specifically, the acoustic driver system is used for MR Elastography and includes a remotely located active acoustic driver and a passive acoustic driver. The active driver includes a diaphragm mounted within a chamber and coupled to a linear actuator. The linear actuator reciprocates in response to an applied current causing the diaphragm to produce oscillating acoustic energy. The passive driver includes a housing defining an enclosed space when positioned on a subject being imaged. The active driver and passive driver are acoustically coupled by a tube having one end connected to the passive driver and a second end connected to the active driver. Oscillating acoustic energy produced by the active driver is directed through the tube to the passive driver and applied to the subject being imaged. A corresponding vibratory force is produced in the subject during the imaging procedure.

A general object of this invention is to produce pressure waves for an acoustic driver system that are high enough in magnitude to produce shear waves over a large region of interest within the subject being imaged. By using an active driver that employs a stiff diaphragm having a compliant perimeter that reciprocates with a long stroke, oscillating pressure waves can be produced at higher magnitudes.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 4 is a cross-sectional view of another implementation of a passive driver which forms part of the system of FIG. 1; and FIG. 5 is a cross-sectional view of yet another implementation of a passive driver which forms part of the system of FIG. 1.

DETAILED DESCRIPTION OF THE PREFERRED EMBODIMENT

By observing the rate at which the strain decreases as a function of distance from the stress producing source, the attenuation of the strain wave can be estimated. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

Figure 1:
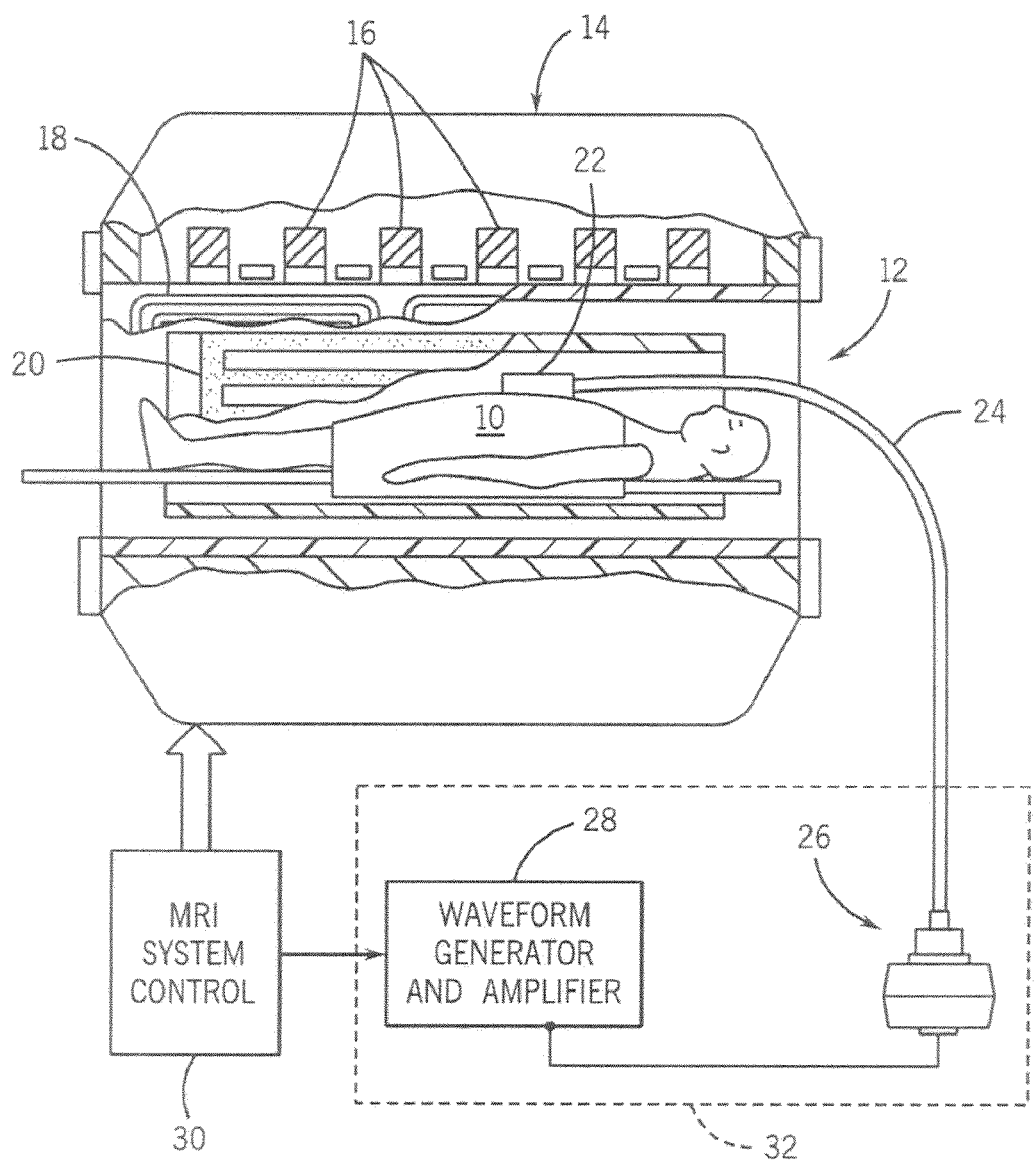
FIG. 1 is a pictorial representation of an MRI system which employs a an implementation of the present system.

The present invention is employed in a system such as that described in the previously cited U.S. Pat. No. 5,592,085 which provides a means for measuring the strain in gyromagnetic materials, such as tissues, using MR methods and apparatus. Referring to FIG. 1, a subject 10 to be examined is placed in the bore 12 of an MRI system magnet 14 and is subjected to magnetic fields produced by a polarizing coil 16, gradient coils 18 and an RF coil 20 during the acquisition of MR data from a region of interest in the subject 10. The homogeneity of these magnetic fields is important and any objects placed in the bore 12 must be carefully constructed of materials that will not perturb them.

The present invention is an acoustic driver system for MR Elastography, a portion of which is placed on the subject 10 and energized to produce a vibratory stress. The system includes a passive driver 22 positioned over the region of interest in the subject 10 and connected by means of a tube 24 to a remotely located active driver 26. The active driver 26 is remote from the bore 12 of the magnet 14 in the sense that it is away from the strong magnetic fields produced by the magnet 14 where its operation is not impeded by those fields, and where its operation will not perturb the MRI system magnetic fields.

The active driver 26 is electrically controlled by a waveform generator and amplifier 28, which in turn is controlled by a pulse sequencer in the MRI system control 30. The MRI system control 30 directs the MRI system to perform an MRE scan by driving the RF coil 20 and the gradient coils 18 in the magnet assembly 14 to perform a series of pulse sequences. The MRI system control 30 further directs the waveform generator 28 to apply an oscillatory stress to the subject 10 at the proper moment during each pulse sequence as described in the previously cited U.S. Pat. No. 5,592,085. The active driver 26 and the waveform generator and amplifier 28 may be housed together in a portable unit as denoted with a dashed line 32.

Figure 2:
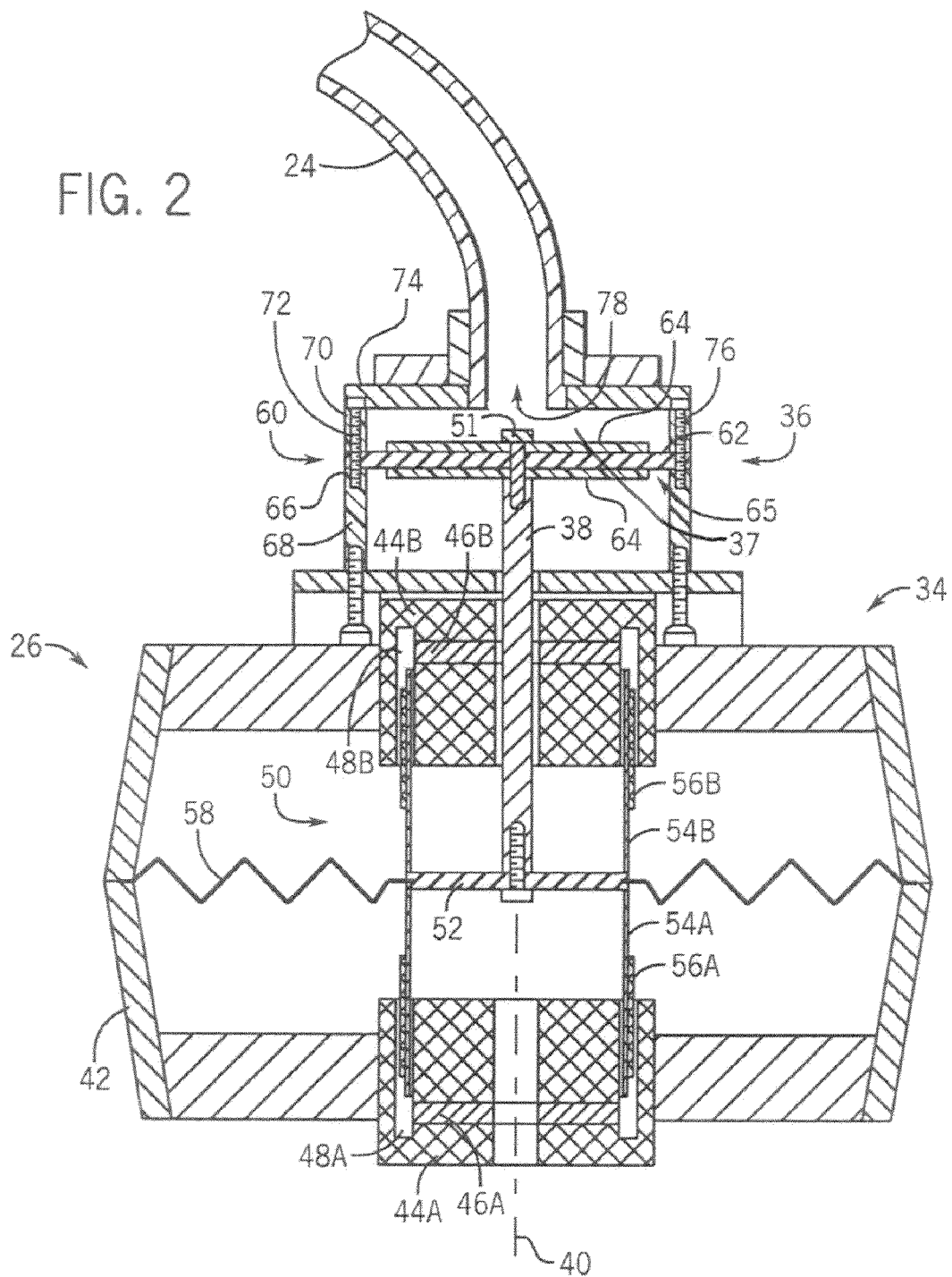
FIG. 2 is a cross-sectional view of one implementation of an active driver used in the system of FIG. 1.

Referring to FIG. 2, the active driver 26 includes a high-powered linear motor 34 mounted to a rigid cylindrical housing 36 concentric about a motor axis 40 and defining a chamber 37. An example linear motor 34 is an electromagnetic linear motor manufactured by CoDrive of Bend, Oregon and sold under the trademark NEOSYM. The motor 34 is described in greater detail in U.S. Pat. No. 6,778,677, entitled "Repairable Electromagnetic Linear Motor For Loudspeakers And The Like". The motor 34 converts alternating current from the waveform generator and amplifier 28 into reciprocating linear motion of a drive rod 38 extending along a motor axis 40.

The motor 34 includes a two piece motor frame 42 and first and second magnet structures 44A, 44B that support annular-shaped permanent magnets 46A, 46B. Each magnet support structure 44A, 44B further includes an annular air gap 48A, 48B respectively. The motor 34 further includes an armature 50, concentric with the motor axis 40, comprised of a central hub 52, cylindrical supports 54A, 54B, and voice coils 56A, 56B. The supports 54A, 54B carry portions of the voice coils 56A, 56B into the air gaps 48A, 48B, respectively. The voice coils 56A, 56B are electrically connected to the waveform generator and amplifier 28 and receive an alternating current therefrom. The armature 50 reciprocates in response to the applied current, the magnitude of which may be varied as desired to alter the displacement of the armature 50.

A single large spider 58 is attached to the armature 50 and acts as a centering support to prevent contact between the voice coils 56A, 56B and the magnet support structures 44A, 44B. The spider 58 further acts as a spring by applying a pulling force to the armature 50 when displaced from a neutral or resting position.

The tubular drive rod 38 is attached to the armature 50 at the central hub 52. The drive rod 38 transfers the reciprocating motion of the armature 50 to a diaphragm 60 situated within the chamber 37 formed by the housing 36. The diaphragm 60 is secured to the drive rod 38 with a screw 51. When actuated, the diaphragm 60 produces acoustical pressure waves, the magnitude of which vary by the amount of displacement of the diaphragm 60.

The diaphragm 60 includes a flat circular piece 62 of silicone rubber sandwiched between two stiffening plates 64. The diameter of the rubber piece 62 is approximately the same as the outer diameter of the housing 36. Each stiffening plate 64 has a diameter less than the diameter of the cylindrical chamber 37 defined by the housing 36. The diaphragm 60 thus includes a rigid portion formed by the stiffening plates 64 and a compliant perimeter 65 formed by the portion of the rubber piece 62 extending radially outward from the plates 64.

The housing 36 includes a lower housing section 68 and an upper housing section 72 which are held together to secure the diaphragm 60 to the housing 36 therebetween. As shown, an outermost portion of the flexible perimeter 65 is compressed between an upper annular surface 66 of the lower housing section 68 and a lower annular surface 70 of the upper housing section 72. The lower housing section 68, diaphragm 60, upper housing section 72, and a ported cover 74 are secured together with a plurality of screws 76 extending therebetween. The diaphragm 60 thus forms an air tight seal within the chamber 37. If the diaphragm 60 becomes fatigued, the housing 36 may be disassembled and a replacement diaphragm 60 used.

In operation, the drive rod 38 is extended and retracted by the linear motor 34 in response to an input current from the waveform generator and amplifier 28. The drive rod 38 is coupled to the diaphragm 60 such that the reciprocal motion of the drive rod 38 along the motor axis 40 reciprocates the diaphragm 60 thereby generating oscillating acoustical pressure waves within the chamber 37.

The diaphragm 60 may have a long stroke of up to +/−2 cm. Depending on the impedance of the load (in this example, the load being the amount of air sealed between the diaphragm 60 and the passive driver 22), the flexing, or displacement, of the diaphragm 60 generates acoustic energy having a certain magnitude which is then delivered to the passive driver 22. Other linear actuators, including one with a "rolling seal" diaphragm or a piston, may be used to produce the reciprocating motion needed to drive the diaphragm assembly.

As shown in FIG. 2, one end of the tube 24 is connected to the housing 36 via an opening 78 formed in the ported cover 74 and acoustically coupled to the chamber 37 defined therein. As a result, acoustic energy produced by the diaphragm 60 is directed through the chamber 37 and into the tube 24.

The tube 24 is made of a material which is flexible, but not elastic. The flexibility enables it to be fed along a winding path between the subject 10 in the magnet 14 and the remote site of the active driver 26. In one implementation the tube 24 is twenty-five feet long and has an inner diameter of one inch. It is made of a clear vinyl material sold under the trademark TYGON and has a wall thickness of approximately one-eighth inch. The tube 24 is inelastic such that it does not expand in response to the variations in air pressure caused by the acoustic energy it conveys. As a result, the acoustic energy is efficiently conveyed from the active driver 26 to the passive driver 22.

Figure 3:
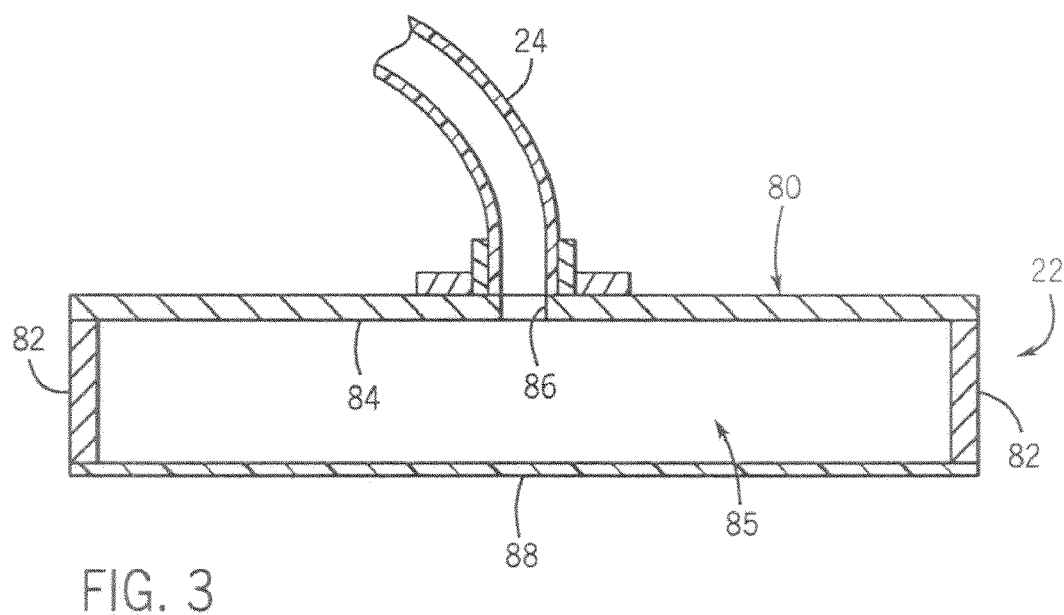
FIG. 3 is a cross-sectional view of one implementation of a passive driver which forms part of the system of FIG. 1.

Referring to FIG. 3, passive driver 22 includes a cylindrical shaped enclosure 80 and a flexible, but not elastic membrane 88. The enclosure 80 is formed with a rigid cylindrical outer wall 82 and a rigid circular end wall 84. One end of the outer wall 82 and the end wall 84 are joined together and define a chamber 85. Both walls 82 and 84 are made of a polycarbonate or other non-ferrous, non-electrically conducting material that is both rigid and relatively "invisible" to the magnetic fields produced in the bore 12 of the magnet 14. The size, shape, and materials of construction of this enclosure 80 depend on the particular clinical application. Enclosures 80 ranging from one to ten inches in diameter have been constructed and tested.

An inlet hole 86 formed in either the outer wall 82 or the end wall 84 acoustically couples the interior of the tube 24 to the chamber 85 defined by the enclosure 80. The membrane 88 is secured across the other end of the cylindrical outer wall 82. In one implementation the membrane 88 is a very thin sheet (e.g., 0.01-0.02 inches or 0.25-0.50 mm thick) of polycarbonate material.

In operation, the flexible membrane 88 is placed against the skin of the subject 10 and vibrates in response to oscillating acoustic energy received from the active driver 26. The vibrations produce an oscillating stress on the skin of the subject 10 which is conveyed into the region of interest as shear waves. Because the space defined by the interior of the tube 24 and each of the chambers 37, 85 is rigidly defined and sealed, the acoustic pressure waves produced by the diaphragm 60 are efficiently conveyed to the membrane 88.

Another configuration of passive driver 122 for use with the active driver 26 of FIG. 3 is shown in FIG. 4 and does not include a membrane. Instead, when placed on the skin 166 of the subject 10, the skin 166 acts as a membrane by vibrating in response to the acoustic energy. As long as an air-tight seal is maintained between the passive driver 122 and the skin 166, acoustic energy is efficiently transferred into the region of interest. Although shown as being relatively compliant, the passive driver 122 may also be rigid and inflexible. Further, the passive driver 122 may have a non-circular shape such as a rectangle.

In FIG. 5 passive driver 222 is constructed entirely from pliable and compressible materials. Such materials allow the passive driver 222 to conform more closely to the anatomical shape of the subject 10 to be imaged, thus alleviating any pressure points and allowing more surface area contact by the passive driver 222. The alternative implementations shown in FIGS. 4 and 5 are described in greater detail in co-pending U.S. application Ser. No. 12/418,204, entitled "Passive Acoustic Driver For Magnetic Resonance Elastography" filed on Apr. 3, 2009.

Because each passive driver is constructed of materials which will not perturb magnetic fields, and because no electric current is required to operate, each of the passive drivers can be freely located anywhere within the bore 12 of the magnet 14. There is no need to align them in any particular direction to operate, and they can be placed very close to the region of interest without producing image artifacts.

The present invention produces an oscillatory stress at a level that is much larger than produced by prior art drivers, including other pressure-actuated drivers. Unlike the prior art pressure actuated drivers, the present system produces and delivers large amounts of oscillating stress in the form of acoustic pressure waves regardless of the impedance of the load.

While the acoustic driver system is specifically designed for use with an MRI system, it may also be used with other imaging modalities. For example, ultrasound strain imaging methods use ultrasound to detect motion of tissues in response to the application of oscillatory stress. The present invention is better able to produce such oscillatory stress in tissues located deep within the subject.

The invention claimed is:

1. A driver for producing an oscillatory stress in a subject undergoing an imaging examination comprising:
   a passive driver having an enclosure defining an enclosed space when positioned on the subject;
   a tube having a first end coupled to the passive driver and extending from the first end to a second end and enclosing an elongated space in communication with the enclosed space defined by the passive driver;
   an active driver coupled to the second end of the tube and having a housing defining a chamber in communication with the elongated space in the tube, the active driver including:
      a linear actuator having an armature that reciprocates in response to an alternating current applied to an actuator coil,
      a diaphragm mounted for reciprocating motion within the chamber, and
      a drive rod connecting the armature to the diaphragm to cause the diaphragm to produce pressure waves directed through the tube to the passive driver when the diaphragm is stroked.

2. The driver as recited in claim 1 in which the diaphragm is comprised of a rigid element having a flexible perimeter and wherein a portion of the flexible perimeter is secured to the housing.

3. The driver as recited in claim 2 in which the diaphragm forms an air-tight seal within the chamber.

4. The driver as recited in claim 2 in which the rigid element is comprised of a flat rigid piece and the flexible perimeter is comprised of a flat flexible piece, wherein the flexible piece is coaxially aligned with the flat rigid piece, and a portion of the flexible piece extends radially outward from the rigid piece.

5. The driver as recited in claim 4 in which the flexible piece is formed of rubber.

6. The driver as recited in claim 4, in which the active driver housing has a cylindrical shape and the flexible piece has a circular perimeter such that the flexible piece engages the cylindrical housing.

7. The driver as recited in claim 1 in which the diaphragm has a displacement about a motor axis of about ±2 cm when stroked.

8. The driver as recited in claim 1 in which the enclosure of the passive driver includes an opening formed therein configured to form a seal between the housing and a subject when the opening is placed against the skin of the subject.

9. The driver as recited in claim 8 in which the pressure waves are directed to the subject through the opening and the skin acts as a membrane to vibrate tissue therebeneath in response to the pressure waves.

10. The driver as recited in claim 1 in which the passive driver and the tube are made of materials which do not substantially perturb magnetic fields produced by an MRI system.

11. A driver for use with a medical imaging system comprising:
   an active driver operable to produce oscillating acoustic energy in response to an applied waveform signal, the active driver having a housing that defines a chamber and having a diaphragm secured within the housing and being configured to oscillate within this chamber in response to the activation of a linear actuator that is coupled to the diaphragm;
   a passive driver operable to deliver the oscillating acoustic energy to a subject being imaged, the passive driver formed of materials that do not disturb energy waves produced by the imaging system and having a housing configured to define an enclosed space when positioned on the subject;
   a tube having a first end connected to the active driver and a second end connected to the passive driver, wherein the tube is operable to transfer the acoustic energy from the active driver to the passive driver.

12. The driver as recited in claim 11 in which the diaphragm includes a flexible perimeter, wherein the diaphragm forms an air tight seal within the chamber.

13. The driver as recited in claim 11 in which the linear actuator is a linear motor.

14. The driver as recited in claim 11 in which the enclosure of the passive driver has an opening formed therein, wherein the oscillating acoustic energy is directed through the opening and to the skin of the subject being imaged to produce vibrations in the subject.

15. The driver as recited in claim 11 in which the housing has a cylindrical shape and the diaphragm includes a flat rigid plate coupled to a flexible piece, wherein the flexible piece extends radially outward from the rigid plate and is coupled to the housing.

16. An active driver for producing pressure waves that are conveyed to a passive driver positioned on a subject undergoing an imaging procedure comprising:
   a housing defining a chamber;
   a diaphragm mounted in the chamber for reciprocating motion along a motor axis;
   a linear motor mounted to the housing and being operable to produce reciprocating linear motion along with the motor axis in response to an applied electrical current; and
   a drive rod coupled between the diaphragm and the linear motor,
   wherein pressure waves are produced by the diaphragm when it is reciprocated by the linear motor, and the pressure waves are conveyed to the passive driver through an opening in the housing.

17. The active driver as recited in claim 16 in which the housing has a cylindrical wall concentric about the motor axis and the diaphragm has a circular perimeter that remains engaged to the cylindrical wall as it reciprocates within the chamber.

18. The active driver as recited in claim 17 in which the diaphragm has a flexible piece that extends radially outward therefrom to engage the housing.

19. The active driver as recited in claim 17 in which the diaphragm has a stroke of approximately 2 cm.

* * * * *